United States Patent
Tiefenthal et al.

(10) Patent No.: US 6,506,179 B1
(45) Date of Patent: Jan. 14, 2003

(54) TUBE HAVING A RETENTION MEMBER

(75) Inventors: James L. Tiefenthal, Dublin, OH (US); George C. Proicou, Gahanna, OH (US)

(73) Assignee: Abbott Laboratories, Abbott Park, IL (US)

(*) Notice: Subject to any disclaimer, the term of this patent is extended or adjusted under 35 U.S.C. 154(b) by 0 days.

(21) Appl. No.: 09/976,999

(22) Filed: Oct. 12, 2001

(51) Int. Cl.⁷ .................. A61M 31/00; A61M 37/00
(52) U.S. Cl. ............. 604/103.06; 604/104; 604/915; 604/96.01; 604/103.14
(58) Field of Search .................. 604/103, 104, 604/96.01–103.14, 915–921; 128/207.15; 606/192, 194

(56) References Cited

U.S. PATENT DOCUMENTS

| 5,042,976 A | * | 8/1991 | Ishitsu et al. ........... 604/915 |
| 5,057,093 A | | 10/1991 | Clegg et al. ........... 604/283 |
| 5,997,546 A | * | 12/1999 | Foster et al. .......... 604/96.01 |

* cited by examiner

Primary Examiner—Michael J. Hayes
(74) Attorney, Agent, or Firm—Brian R. Woodworth; Michael R. Crabb

(57) ABSTRACT

A retention member and a feeding tube having a feeding lumen and an inflation lumen. The retention member including a sleeve section, an expandable section, and a shoulder section of decreasing wall thickness therebetween. The sleeve section sealingly engages the feeding tube distal end and the expandable section everts about the shoulder section to sealingly engage the feeding tube and define an expandable lumen in communication with the inflation lumen.

8 Claims, 2 Drawing Sheets

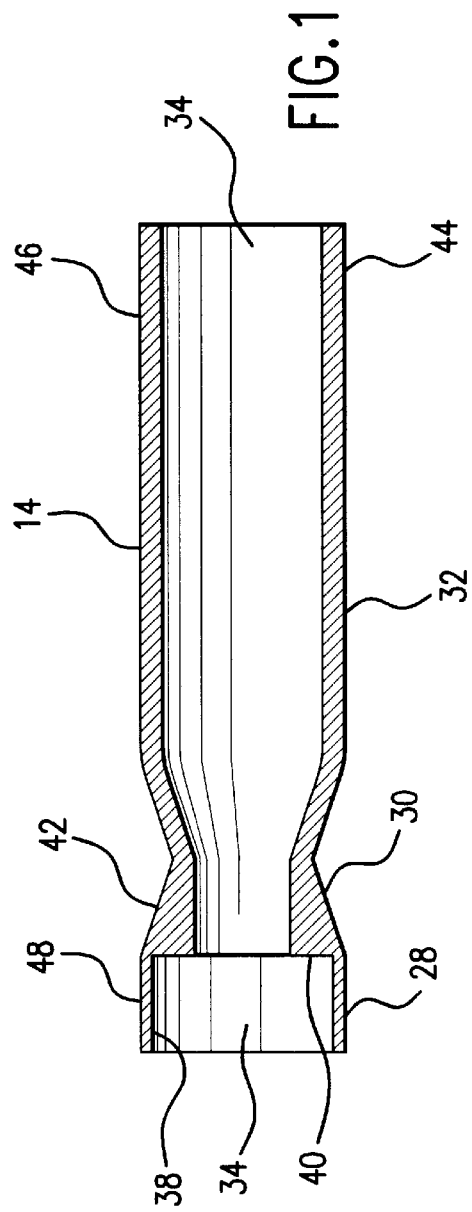
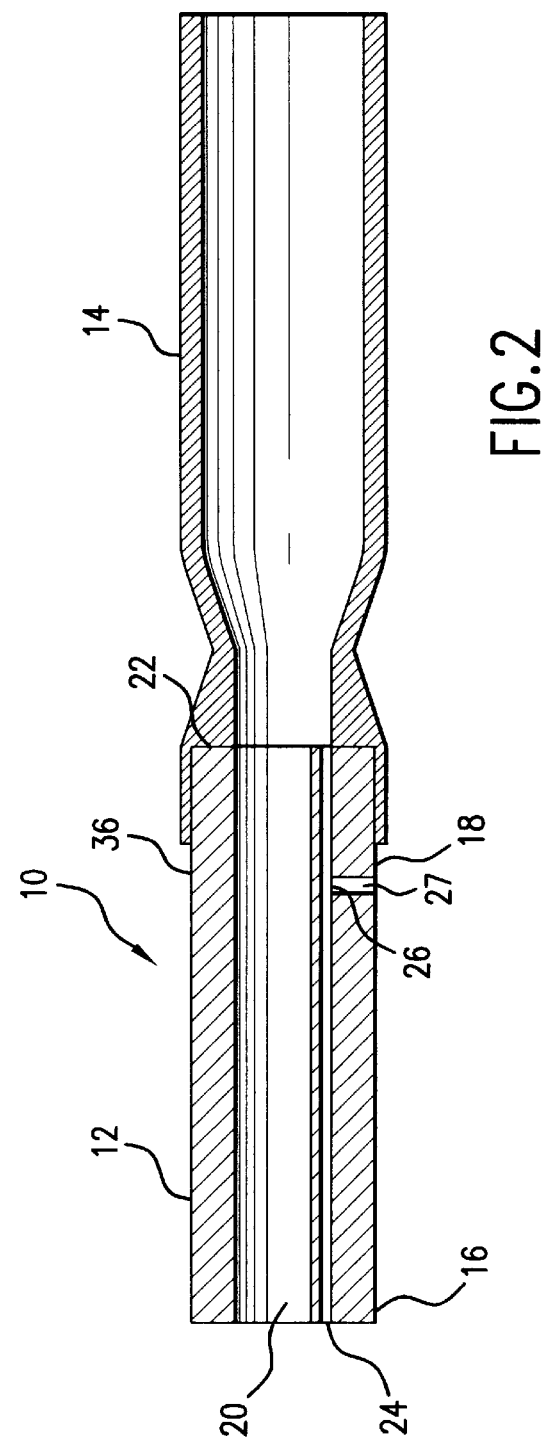

TUBE HAVING A RETENTION MEMBER

TECHNICAL FIELD

This invention relates to tube having an expandable retention member. In particular, the present invention relates to a tube having an expandable member configured such that, when in an expanded condition, the expandable member decreases the incidence of irritation caused by a distal tip of the tube.

BACKGROUND OF THE INVENTION

Tubes having expandable members associated therewith are used for a variety of purposes. For example, catheters having inflatable members disposed on a distal end portion thereof are used in angioplasty procedures and in the placement of stents in a patient's vasculature. Such catheters also are used in other cardiology applications, including the removable positioning of diagnostic equipment in a patient's vasculature.

Tubes having expandable members associated therewith also are used as gastrostomy tubes. Gastrostomy tubes are used to deliver enteral nutritional products to the gastrointestinal tract of a patient. Gastrostomy tubes are positioned such that an enteral nutritional product is delivered percutaneously through a stoma tract from an external source directly to the patient's stomach or small bowel. Gastrostomy tubes preferably have expandable retention members mounted thereon, the retention members being constructed to prevent inadvertent removal of the gastrostomy tube from the patient's stomach.

Retention members preferably are movable between a contracted state and an expanded state. When in the contracted state, the retention member does not prevent the positioning of the catheter or feeding tube in a patient. When the catheter or feeding tube is properly positioned within the patient, the retention member can be placed in its expanded position in order to retain the catheter or feeding tube in the desired position. For example, a portion of a gastrostomy tube can be inserted percutaneously through a patient's abdominal wall into the patient's stomach through a stoma tract formed through known techniques. After the retention member has been properly positioned in the patient's stomach, the retention member is reconfigured into its expanded state in which the external diameter of the retention member is larger than the diameter of the stoma tract, thereby precluding inadvertent withdrawal of the retention member from the patient's stomach.

Many gastrostomy tubes include an inflatable balloon on the distal end of the feeding tube, the inflatable balloon acting as the retention member. The balloon can be selectively expanded by the introduction of an inflation fluid through an inflation lumen associated with the feeding tube in order to reconfigure the retention member from its contracted state to its expanded state. The inflation fluid can then be withdrawn from the balloon in order to reconfigure the retention member to its contracted state.

It has been found that the distal tip of gastrostomy tubes can come into contact with the interior wall of the patient's gastrointestinal tract at a position opposite the stoma tract during normal usage, thereby causing irritation to the gastric mucosa. In order to prevent this irritation from occurring, some retention members have been designed such that they provide a cushion between the distal tip of the feeding tube and the gastrointestinal tract.

For example, U.S. Pat. No. 5,997,546 to Foster, et al. discloses a feeding tube having a retention member that is constructed to cover the distal tip of the feeding tube with an inflatable balloon retention member. When the retention member is in its inflated or expanded configuration, the balloon acts as a cushion between the distal tip of the feeding tube and the patient's gastrointestinal tract. However, due to the fact that the retention member taught by Foster, et al. is attached to an interior wall of the feeding tube, the retention member tends to constrict the distal feeding tube opening defined by the distal tip of the feeding tube, thereby limiting flow through the feeding tube. Further, because the retention member taught by Foster, et al. is attached to an interior wall of the feeding tube, the cost of manufacturing such a feeding tube is substantially higher than the cost of manufacturing other feeding tubes.

SUMMARY OF THE INVENTION

In accordance with one aspect of the present invention, a medical device including a tube and a retention member is provided. The tube has a proximal end portion and a distal end portion, the distal end portion including a distal tip. The tube defines a primary lumen therethrough from its proximal end portion to the distal tip. The tube also defines an inflation lumen therethrough from the proximal end portion to a first point on the distal end portion, the first point being spaced from the distal tip of the tube. The tube has an exterior wall and an interior wall, the interior wall being adjacent to the primary lumen defined through the tube.

The retention member defines a lumen therethrough. The retention member includes a sleeve section, a shoulder section, and an expandable section. The sleeve section sealingly engages the exterior wall of the tube along the distal end portion of the tube proximal the distal tip of the tube. The shoulder section extends from the sleeve section. The shoulder section engages the distal tip of the tube. The expandable section extends from the shoulder section. The expandable section is everted about the shoulder section of the retention member, about the sleeve section of the retention member, and about at least a portion of the distal end portion of the tube. The expandable section sealingly engages the exterior wall of the tube along the distal end portion of the tube to define an expandable lumen between the exterior wall of the tube and the expandable section of the retention member. The inflation lumen defined by the tube is in fluid communication with the expandable lumen defined by the exterior wall of the tube and the expandable section of the retention member at the first point on the distal end portion of the tube.

In accordance with a second aspect of the present invention, a retention member for a tube is provided. The retention member defines a lumen therethrough and includes a sleeve section, a shoulder section, and an expandable section. The sleeve section is constructed to sealingly engage an exterior wall of a distal end portion of a feeding tube proximate a distal tip of the tube. The shoulder section extends from the sleeve section and is constructed to engage the distal tip of the tube. The expandable section extends from the shoulder section and is constructed to be everted about the shoulder section of the retention member and the sleeve section of the retention member. The expandable section of the retention member is constructed to sealingly engage the exterior wall of the tube along the distal end portion thereof.

BRIEF DESCRIPTION OF THE DRAWINGS

In the accompanying drawings that form part of the specification, and in which like numerals are employed to designate like parts throughout the same:

FIG. 1 is a cross-sectional view of a retention member constructed in accordance with the present invention;

FIG. 2 is a cross-sectional view of a feeding tube constructed in accordance with the present invention.

DESCRIPTION OF THE PREFERRED EMBODIMENT

Figure 3:
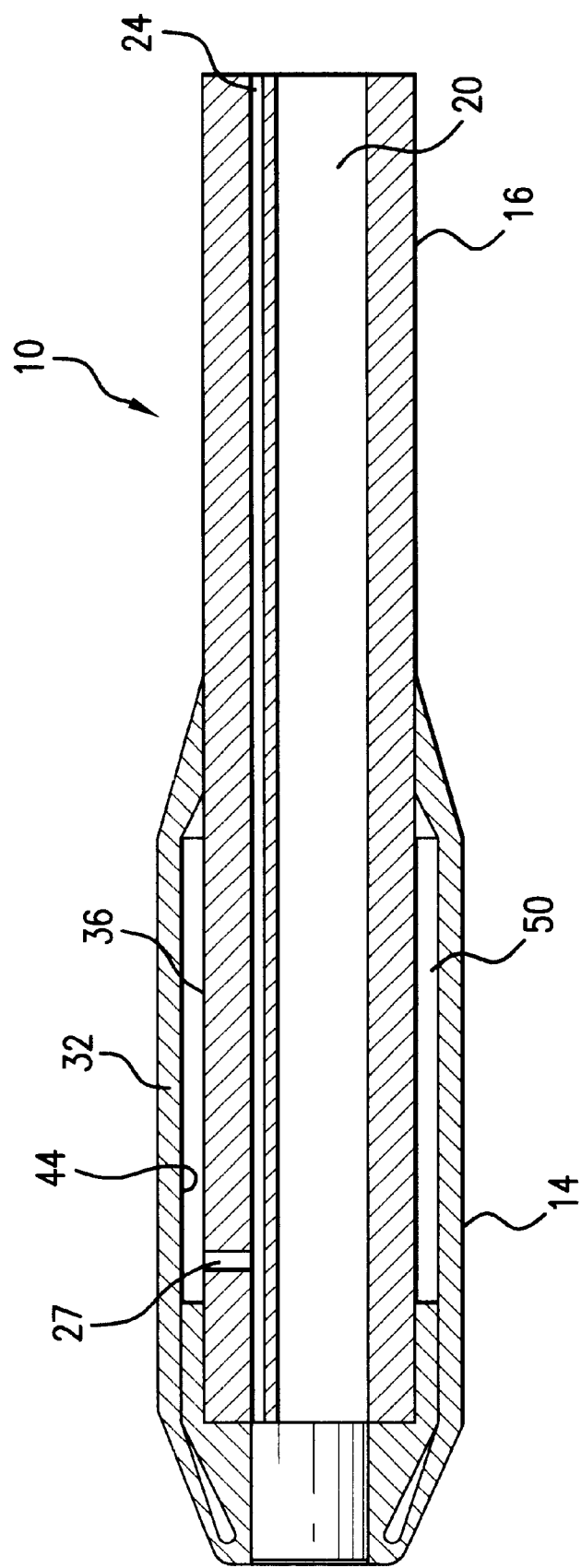
FIG. 3 is a cross-sectional view of a feeding tube constructed in accordance with the present invention and having the expandable section thereof everted to define an expandable lumen.

While this invention is susceptible of embodiment in many different forms, this specification and the accompanying drawings disclose only one specific form as an example of the invention. The invention is not intended to be limited to the embodiment so described. The scope of the invention is pointed out in the appended claims.

The figures illustrating the apparatus show some elements that are known and that will be recognized by one skilled in the art. The detailed descriptions of such elements are not necessary to an understanding of the invention, and accordingly, are herein presented only to the degree necessary to facilitate an understanding of the novel features of the present invention.

The apparatus of this invention is used with certain conventional components the details of which, although not fully illustrated or described, will be apparent to those having skill in the art and an understanding of the necessary functions of such components.

Although the present invention will be described herein in connection with a feeding tube embodiment, it is to be appreciated that the present invention has other medical applications. For example, the present invention can be used in connection with a catheter having an expandable member associated therewith, where the expandable member is constructed to (i) perform an angioplasty procedure; (ii) place a stent in a patient's vasculature; or (iii) temporarily retain a catheter in position within a patient's vasculature.

A feeding tube constructed in accordance with the present invention is generally indicated at 10 in FIG. 2. As depicted in detail in the accompanying figures, feeding tube 10 includes tube 12 and retention member 14. Tube 12 has a proximal end portion 16 and a distal end portion 18. Tube 12 defines a feeding lumen 20 therethrough from the proximal end portion 16 to a distal tip 22 of tube 12. In the embodiment depicted in the accompanying figures, feeding lumen 20 has a substantially circular cross-section and distal tip 22 of tube 12 has a substantially annular cross-section. However, it is to be appreciated that feeding lumen 20 and distal tip 22 of tube 12 can have a variety of configurations, all of which are intended to be within the scope of the present invention described in the accompanying claims. For example, feeding lumen 20 can have a substantially semicircular or D-shaped cross-section.

Tube 12 also defines an inflation lumen 24 therethrough. Inflation lumen 24 extends from proximal end portion 16 of tube 12 to point 26 on distal end portion 18 of tube 12.

Proximal end portion 16 of tube 12 is configured such that feeding lumen 20 can be fluidly connected to a source of enteral nutritional product, thereby allowing the enteral nutritional product to be directed from the source, through the feeding lumen 20, and outwardly from tube 12 at distal tip 22 of tube 12. Proximal end portion 16 of tube 12 also is configured such that inflation lumen 24 can be fluidly connected to a source of inflation fluid, thereby allowing the inflation fluid to be introduced into the inflation lumen 24 and withdrawn from inflation lumen 24 in order to expand and contract an inflatable retention member mounted on distal end portion 18, the inflatable retention member to be described in detail herein.

Proximal end portion 16 can have a variety of known configurations and can include a variety of known features. For example, proximal end portion 16 of tube 12 can include one or more one-way valve members in order to prevent inadvertent backflow of enteral nutritional product through feeding lumen 20 or inflation fluid through inflation lumen 24. Proximal end portion 16 of tube 12 also can include one or more plug members that can be used to selectively seal feeding lumen 20 and/or inflation lumen 24 from an external environment of tube 12 when tube 12 is not fluidly connected to a source of enteral nutritional product or to a source of inflation fluid. U.S. Pat. No. 5,057,093 to Clegg, et al. discloses a Y-shaped adapter that could be connected to proximal end 16 of feeding tube 10 of the present invention. U.S. Pat. No. 5,057,093 is incorporated herein in its entirety by reference. The Y-shaped adapter of U.S. Pat. No. 5,057,093 can be frictionally attached to proximal end 16 of tube 12. Alternatively, the adapter can be bonded to proximal end 16 of tube 12 using known bonding techniques.

Tube 12 can be constructed of variety of known materials. For example, tube 12 can be constructed of known silicone or polyurethane materials, or combinations thereof. Tube 12 can be injection molded or extruded.

Tube 12 of the present invention can be constructed using a variety of known techniques, including extrusion and molding. For example, a dual lumen tube can be extruded from a silicone material, e.g., Dow Q7-4750 silicone, the resulting tube defining both feeding lumen 20 and inflation lumen 24. If desired, a radiopaque strip can be co-extruded with tube 12, thereby allowing tube 12 to be visually identified using known radiography techniques. The resulting dual lumen silicone tube 12 is cut to a desired length, and a scive cut 27 is made in the extruded tube 12 at a point 26 spaced from distal tip 22 of tube 12, e.g., approximately one centimeter from the distal end of the tube. The scive cut 27 is made such that fluid communication is established between an external environment of tube 12 and inflation lumen 24 of tube 12. Silicone or any other appropriate plug material is then inserted into inflation lumen 24 through distal tip 22 of tube 12 in order to seal the inflation lumen 24 between distal tip 22 and scive cut 27. When plugging inflation lumen 24, care should be exercised such that a fluid flow path is maintained between inflation lumen 24 and an external environment of tube 12 through the scive cut 27 at point 26 on tube 12. The purpose of scive cut 27 will be explained below with respect to retention member 14 of the present invention.

Retention member 14 is depicted in detail in FIG. 1. Retention member 14 includes sleeve section 28, shoulder section 30, and expandable section 32. Retention member 14 can be constructed of a variety of known materials, including silicone and polyurethane materials, and combinations thereof. Due to the configuration of retention member 14 of the present invention, retention member 14 preferably is injection molded using known techniques.

Retention member 14 defines a lumen 34 therethrough and is mounted on distal end portion 18 of tube 12 such that lumen 34 is in fluid communication with feed lumen 20 defined by tube 12.

Sleeve section 28 of retention member 14 is configured such that it can be placed into contact with exterior wall 36 of tube 12. In the embodiment depicted in the accompanying figures, sleeve section 28 engages exterior wall 36 of tube 12 along distal end portion 18 of tube 12 proximate distal tip 22 of tube 12. The length of sleeve section 28 can be varied without departing from the scope of the present invention. However, it is preferable that the length of sleeve section 28 be selected such that scive cut 27 at point 26 is not covered by sleeve section 28 of retention member 14, thereby maintaining fluid communication between inflation lumen 24 and an external environment of tube 12 through scive cut 27. If sleeve section 28 is dimensioned such that it covers scive cut 27 at point 26, scive cut 27 can be extended through sleeve section 28 using known techniques in order to maintain fluid communication between inflation lumen 24 and an external environment of tube 12 through the scive cut 27 at point 26 on tube 12.

It will be appreciated that the configuration of sleeve section 28 preferably matches the configuration of tube 12 at distal end portion 18 thereof. In the embodiment of the present invention depicted in the accompanying figures, distal end portion 18 of tube 12 has a circular exterior wall 36, thus sleeve section 28 is substantially annular in shape and has an inner wall 38 that is configured and dimensioned to engage exterior wall 36 of distal end portion 18 or tube 12. It also will be appreciated that sleeve section 28 will not interfere with the flow of enteral nutritional product through feed lumen 20 at distal tip 22 because sleeve section 28 engages exterior wall 36 of tube 12.

Sleeve section 28 can be frictionally mounted on distal end portion 18 of tube 12 by way of a slip fit or friction fit therebetween. Alternatively, sleeve section 28 can be bonded to exterior wall 36 of tube 12 using known bonding techniques. For example, known adhesive bonding techniques and known solvent bonding techniques can be used to bond sleeve section 28 to exterior wall 36 of tube 12. Sleeve section 28 also can be heat bonded onto exterior wall 36 of tube 12 using known techniques. The selected bonding technique will be dependent upon (a) the respective materials of construction for tube 12 and retention member 14; and (b) the desired strength of attachment between tube 12 and retention member 14. For example, where retention member 14 and tube 12 are both formed from silicone, an RTV silicone material can be used to bond retention member 14 and tube 12.

Shoulder section 30 extends from sleeve section 28 of retention member 14 as depicted in the accompanying figures. Shoulder section 30 includes an engagement surface 40 which is constructed to engage distal tip 22 of tube 12. The configuration of shoulder section 30 also is selected to be complementary to the configuration of tube 12. In the accompanying figures, shoulder section 30 and engagement surface 40 are annular in configuration in order to complement the circular exterior wall 36 of tube 12 and the annular configuration of distal tip 22. The thickness of shoulder section 30 at engagement surface 40 is preferably equal to or less than the wall thickness of distal tip 22 of tube 12, thereby ensuring that engagement surface 40 of shoulder section 30 does not interfere with the flow of enteral nutritional product through feed lumen 20 at distal tip 22 of tube 12.

Although it is not necessary, engagement surface 40 of shoulder section 30 can be bonded to distal tip 22 of tube 12 using known bonding techniques. For example, an appropriate adhesive material can be selected in order to adhesively bond engagement surface 40 to distal tip 22 of tube 12. Engagement surface 40 also can be heat bonded onto exterior tip 22 of tube 12 using known techniques. As above-discussed, the selected bonding technique will be dependent upon (a) the respective materials of construction for tube 12 and retention member 14; and (b) the desired strength of attachment between tube 12 and retention member 14. For example, where retention member 14 and tube 12 are both formed from silicone, an RTV silicone material can be used to bond engagement surface 40 and distal tip 22.

The wall thickness of shoulder section 30 at distal end 42 of shoulder section 30 is selected such that distal end 42 is more flexible than distal tip 22 of tube 12. Thus, distal end 42 of shoulder section 30 is less likely to cause irritation to a patient's gastric mucosa than is distal tip 22. The wall thickness of distal end 42 of shoulder section 30 will be selected based upon (a) the desired degree of flexibility at distal end 42; and (b) the material used to construct retention member 14 of the present invention.

The configuration of shoulder section 30 depicted in the accompanying figures provides a distal end 42 of shoulder section 30 that has a reduced wall thickness compared to the wall thickness of engagement surface 40. The wall thickness of shoulder section 30 can be substantially constant along its length. For example, the thickness of the shoulder section 30 along its length can be the reduced wall thickness depicted at distal end 42. Alternatively, the thickness of shoulder section 30 along its length can be the thickness of the engagement surface 40, which is approximately the same as the thickness of tube 12 at distal tip 22.

In the embodiment of shoulder section 30 depicted in the accompanying drawings, the wall thickness of shoulder section 30 decreases from engagement surface 40 to distal end 42, with the largest wall thickness being adjacent to engagement surface 40 and the smallest wall thickness being at the distal end 42 of shoulder section 30. This configuration of shoulder section 30 exhibits greater hoop strength than does an embodiment in which the wall thickness of shoulder section 30 is less than the wall thickness of tube 12 at distal tip 22 along the entire length of shoulder section 30, while simultaneously providing a distal end 42 of shoulder section 30 that is more flexible than distal tip 22 of tube 12.

It should be noted that lumen 34 defined by shoulder section 30 is substantially constant in dimension along the length of shoulder section 30 in the embodiment of the present invention depicted in the accompanying figures. That is, the decrease in wall thickness of shoulder section 30 from engagement surface 40 to distal end 42 is achieved by tapering the outside surface of shoulder section 30. Lumen 34 defined by shoulder section 30 thus does not impede the flow of enteral nutritional product through feed lumen 20 of tube 12.

Expandable section 32 of retention member 14 extends from shoulder section 30 at distal end 42 of shoulder section 30. Expandable section 32 is constructed such that it can be averted over shoulder section 30, sleeve section 28, and at least a portion of distal end portion 18 of tube 12. Exterior surface 44 of expandable section 32 faces shoulder section 30, sleeve section 28, and at least a portion of distal end portion 18 of tube 12 after expandable section 32 has been everted. A portion of exterior surface 44 of distal end portion 46 of expandable section 32 is then brought into sealing engagement with a section of distal end portion 18 of tube 12 such that distal end portion 18 of tube 12, sleeve portion 28, shoulder section 30, and expandable section 32 define an expandable lumen 50 (FIG. 3) in fluid communication with inflation lumen 24 through scive cut 27. If scive cut 27 extends through sleeve section 28 as above discussed, exterior surface 44 of distal end portion 46 of expandable section 32 can sealingly engage outer wall 48 of sleeve section 28. If desired, exterior surface 44 of distal end portion 46 of expandable section 32 can sealingly engage both outer wall 48 of sleeve section 28 and exterior wall 36 of tube 12 at distal end portion 22 again, provided that the expandable lumen 50 Is in fluid communication with inflation lumen 24 through scive cut 27.

Exterior surface 44 of distal end portion 46 of expandable section 32 can be made to sealingly engage exterior wall of distal end portion 18 and/or outer wall 48 of sleeve section 28 using a variety of known bonding techniques, including adhesive bonding, solvent bonding, heat bonding, and/or RTV silicone bonding.

As above-discussed, the point at which expandable section 32 is caused to sealingly engage tube 12 Is selected such that expandable lumen 50 is in fluid communication with inflation lumen 24 of tube 12 through scive cut 27. Upon the introduction of a fluid into inflation lumen 24 of tube 12 at proximal end portion 16 of tube 12, the inflation lumen will flow into expandable lumen 50, thereby causing expandable section 32 to distend radially outwardly from tube 12. Because expandable section 32 of retention member 14 extends directly from distal end 42 of shoulder section 30, and because the above-referenced hoop stress characteristic of shoulder section 30 of the present invention, the distention of expandable section 32 will not tend to diminish the size of the lumen defined 34 retention member 14, and therefore does the lumen defined 34 retention member 14, and therefore does not impede the flow of an enteral nutritional product through feed lumen 20 of tube 12. It also has been found that the elongation of retention member 14 is minimal upon distention of expandable section 32 when compared to prior art devices of this type. This feature of the feeding tube of the present invention, coupled with the relative flexibility of distal end 42 of shoulder section 30, serves to minimize the likelihood that feeding tube 10 of the present invention will cause irritation to a patient's gastrointestinal tract.

Although the present invention has been described herein in the context of certain embodiments, one of ordinary skill in the art will recognize that various modifications can be made to such embodiments. Such modifications are considered to be within the scope of the appended claims which are intended to set forth the scope of the present invention.

What is claimed is:

1. A medical device comprising:
    a tube having a proximal end portion and a distal end portion, said distal end portion including a distal tip, said tube defining a feeding lumen therethrough from said proximal end portion to said distal tip, said tube defining an inflation lumen therethrough from said proximal end portion to a first point on said distal end portion spaced from said distal tip, said tube having an exterior wall and an interior wall, said interior wall being adjacent to said feeding lumen defined through said tube;
    a retention member defining a lumen therethrough, said retention member comprising a sleeve section, a shoulder section, and an expandable section, said sleeve section sealingly engaging said exterior wall of said tube along said distal end portion of said tube proximal said distal tip of said tube, said shoulder section extending from said sleeve section, said shoulder section having an engagement surface engaging said distal tip of said tube, said expandable section extending from said shoulder section, said expandable section being everted about said shoulder section of said retention member, said sleeve section of said retention member, and at least a portion of said distal end portion of said tube, said expandable section sealingly engaging said exterior wall of said tube along said distal end portion of said tube to define an expandable lumen between said exterior wall of said tube and said expandable section of said retention member, said inflation lumen defined by said tube being in fluid communication with said expandable lumen defined by said exterior wall of said tube and said expandable section of said retention member at said first point on said distal end portion of said tube;
    wherein said shoulder section of said retention member has a wall thickness, and wherein said wall thickness of said shoulder section decreases from said sleeve section to said expandable section of said retention member.

2. A feeding tube in accordance with claim 1, wherein said tube is constructed from a material comprising a silicone material.

3. A feeding tube in accordance with claim 1, wherein said tube is constructed from a material comprising a polyurethane material.

4. A feeding tube in accordance with claim 1, wherein said retention member is constructed from a material comprising a silicone material.

5. A feeding tube in accordance with claim 1, wherein said retention member is constructed from a material comprising a polyurethane material.

6. A retention member for a medical device, said retention member comprising:
    a retention member comprising a sleeve section, a shoulder section, and an expandable section, said sleeve section constructed to sealingly engage an exterior wall of a distal end portion of a tube proximate a distal tip of the feeding tube, said shoulder section extending from said sleeve section, said shoulder section constructed to engage the distal tip of the feeding tube, said expandable section extending from said shoulder section, said expandable section being evertable about said shoulder section of said retention member and said sleeve section of said retention member and said sleeve section of said retention member, said expandable section of said retention member constructed to sealingly engage the exterior wall of the tube along the distal end portion of the tube;
    wherein said shoulder section of said retention member has a decreasing wall thickness from said sleeve section to said expandable section of said retention member.

7. A retention member in accordance with claim 6, wherein said retention member is constructed from a material comprising a silicone material.

8. A retention member in accordance with claim 7, wherein said retention member is constructed from a material comprising a polyurethane material.

\* \* \* \* \*

UNITED STATES PATENT AND TRADEMARK OFFICE
CERTIFICATE OF CORRECTION

PATENT NO.    : 6,506,179 B1
DATED         : January 14, 2003
INVENTOR(S)   : James L. Tiefenthal et al.

It is certified that error appears in the above-identified patent and that said Letters Patent is hereby corrected as shown below:

<u>Column 8,</u>
Line 58, replace "Claim 7" with -- Claim 6 --.

Signed and Sealed this

Fifth Day of August, 2003

JAMES E. ROGAN
*Director of the United States Patent and Trademark Office*